United States Patent
Austin et al.

(10) Patent No.: US 7,096,554 B2
(45) Date of Patent: Aug. 29, 2006

(54) PROTECTIVE LOADING OF STENTS

(75) Inventors: Michael Austin, Galway (IE); Daniel C. Perreault, Ham Lake, MN (US); Gabriel S. Sobrino, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 668 days.

(21) Appl. No.: 10/407,036

(22) Filed: Apr. 4, 2003

(65) Prior Publication Data

US 2004/0199239 A1    Oct. 7, 2004

(51) Int. Cl.
| B23P 19/04 | (2006.01) |
| A61B 17/00 | (2006.01) |
| A61F 2/06 | (2006.01) |
| B21C 9/00 | (2006.01) |
| B21D 41/00 | (2006.01) |

(52) U.S. Cl. ............... 29/282; 29/283.5; 29/447; 29/515; 29/516; 606/1; 606/108; 604/915; 623/1.42; 72/286; 72/372; 72/402

(58) Field of Classification Search ............ 29/447, 29/271, 282, 508, 515, 516, 234, 283.5; 623/1.19, 623/1.42, 1.46; 606/1, 108; 604/915; 72/285, 72/286, 370.04, 372, 402

See application file for complete search history.

(56) References Cited

U.S. PATENT DOCUMENTS

| 5,992,000 | A | 11/1999 | Humphrey et al. ........... 29/516 |
| 6,063,092 | A * | 5/2000 | Shin ............................ 606/108 |
| 6,063,102 | A | 5/2000 | Morales ...................... 606/198 |
| 6,074,381 | A | 6/2000 | Dinh et al. ..................... 606/1 |
| 6,082,990 | A | 7/2000 | Jackson et al. .............. 425/517 |
| 6,096,027 | A * | 8/2000 | Layne ............................ 606/1 |
| 6,108,886 | A | 8/2000 | Kimes et al. ................. 29/280 |
| 6,309,383 | B1 * | 10/2001 | Campbell et al. ............... 606/1 |
| 6,352,547 | B1 | 3/2002 | Brown et al. |
| 6,360,577 | B1 | 3/2002 | Austin |
| 6,387,117 | B1 | 5/2002 | Arnold, Jr. et al. |
| 6,387,118 | B1 | 5/2002 | Hanson ..................... 623/1.11 |

OTHER PUBLICATIONS

U.S. Appl. No. 09/401,467, filed Sep. 22, 1999, Brown, Klisch, and Shukhat.
U.S. Appl. No. 09/401,213, filed Sep. 22, 1999, Leanna, Elliot, Arnold Jr., Brown, Larson, Ellis, and Dusbabek.
U.S. Appl. No. 09/404,986, filed Sep. 22, 1999, Klisch, Ulanowski, Plessal, Ellis, Dusbabek, Lorentzen, Hanson, Larson, and Brown.
U.S. Appl. No. 09/401,218, filed Sep. 22, 1999, Austin.

* cited by examiner

Primary Examiner—Jermie E. Cozart
(74) Attorney, Agent, or Firm—Vidas, Arrett & Steinkraus (57) ABSTRACT

A system for protecting a stent from contact during loading comprises a stent, a protective sleeve disposed about the stent and a loading tool. The inner diameter of the protective sleeve is greater than the outer diameter of the stent. The protective sleeve has a length longer than that of the stent. The portion of the sleeve extending beyond the length of the stent defines a sleeve extension. The loading tool is positioned about at the stent retaining sleeve of a catheter. The tip region of the loading tool separates the protective sleeve and the stent from one another when the protective sleeve is pulled over the tip region of the loading tool. When the protective sleeve is pulled over the tip region of the loading tool the stent is advanced into a lumen defined by the stent retaining sleeve of the catheter.

37 Claims, 5 Drawing Sheets

PROTECTIVE LOADING OF STENTS

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

The present invention relates generally to stents, stent loading stent contracting and stent delivery systems and their respective methods of use. Some embodiments of the invention are more specifically directed to a removable protective sheath which protects the stent from direct contact with a stent loading and/or stent contracting system. Some embodiments are more specifically directed to stent loading, contracting and/or delivery systems which are configured to accommodate such a protective sleeve and stent.

2. Description of Related Art

A stent is a generally tubular device that is used to support a bodily lumen. A stent is typically delivered to a desired bodily location via a catheter. Often the stent is loaded onto a portion of the catheter, such as a balloon or other region of the catheter shaft. In some stent delivery systems the stent is crimped to the catheter in order to minimize the profile of the stent on the catheter and to prevent undesired movement of the stent relative to the catheter shaft.

A number of techniques for loading and contracting a stent to a catheter shaft or balloon are used. One such technique that is commonly used in the radiological suite involves hand crimping the stent to the balloon. A stent is placed over an uninflated balloon and then squeezed with the fingers until the stent is in intimate contact with the uninflated balloon. The technique is highly operator dependent and can affect stent profile and stent placement with respect to the balloon and radiopaque markers. It can also affect the dilatation length of the stent and lead to pinching of the balloon.

Other techniques for crimping stents involve the use of mechanical devices for crimping stents. Mechanical stent crimpers have been disclosed in a number of patents including U.S. Pat. Nos. 6,387,118; 6,108,886; 6,092,273; 6,082,990; 6,074,381; 6,063,102 and 5,992,000. Mechanical stent crimpers have also been disclosed in a number of copending, commonly assigned patent applications including U.S. application Ser. No. 09/401,467 now U.S. Pat. No. 6,352,547, Ser. No. 09/401,213 now U.S. Pat. No. 6,387,117, Ser. No. 09/404,986 now U.S. Pat. No. 6,769,161, and Ser. No. 09/401,218 now U.S. Pat. No. 6,360,577.

When assembling a catheter for delivery of a stent and for insertion into a body vessel, the stent is loaded onto the catheter. During the loading process the catheter and in some cases the stent is manipulated, often by hand. The manipulation of the catheter may cause the stent to be contacted and potentially damaged. Where the stent includes or is coated with a drug or other material, such contact may disturb the coating and impair the proper delivery thereof. In addition, contacting the stent during the loading and/or crimping process may result in the drug coating of the stent being contaminated with the residue of previous stent coatings that have been previously contacted by the loading and/or crimping system.

Thus, there remains a need to provide a device or mechanism for preventing direct contact between a stent, particularly a drug coated stent, and the tool or system used to load and/or crimp the stent onto the catheter shaft or balloon.

All US patents, applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is embodied in a variety of forms. In at least one embodiment the invention is directed to a crimpable and removable sheath or protector which may be placed onto the stent prior to the loading of the sent on to the catheter and/or crimping of the stent thereon. The protector eliminates direct contact between the loading and/or crimping apparatus and the stent. The stent used with the protector may be any type of implantable medical device. The stent may be a self-expanding, balloon expandable or hybrid stent.

In some embodiments the protector is configured to act as a disposable stent storage capsule. In some embodiments the storage capsule includes a cap assembly with a removable seal. In at least one embodiment the cap assembly is constructed and arranged to cooperatively engage a portion of a catheter assembly in order to accommodate loading of the stent thereon when the cap is unsealed.

In some embodiments the invention is directed to a contracting or crimping mould having one or more contracting apertures or openings which receive and/or draw the slack or folds of the protector which form as the stent is contracted and reduced in diameter. In some embodiments the contracting mould comprises one or more rods, each of which engage a fold of the protector to draw the folds away from the stent during contracting thereby ensuring that the points of contact between the protector and the stent remain free of folding or crinkling.

In at least one embodiment the invention is directed to a stent loading device which is constructed and arranged to be disposed about a stent delivery catheter and engage a free end of the protector. The loading device is configured to move in a linear manner relative to the catheter thereby loading the stent into the catheter while simultaneously removing the protector from about the stent.

In some embodiments a contracting mould, loading device and protector are used in conjunction with each other to reduce and load a stent onto a delivery catheter.

In at least one embodiment the stent is cooled prior to being loaded onto the catheter.

In at least one embodiment the protector comprises a heat shrink material. In some embodiments the heat shrink protector is heated as the stent is cooled, or subsequently thereto. In some embodiments the contracting mould comprises a cooling mechanism for cooling the stent and a heating mechanism for heating the heat shrinkable protector during the contraction of the stent.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

Figure 1:
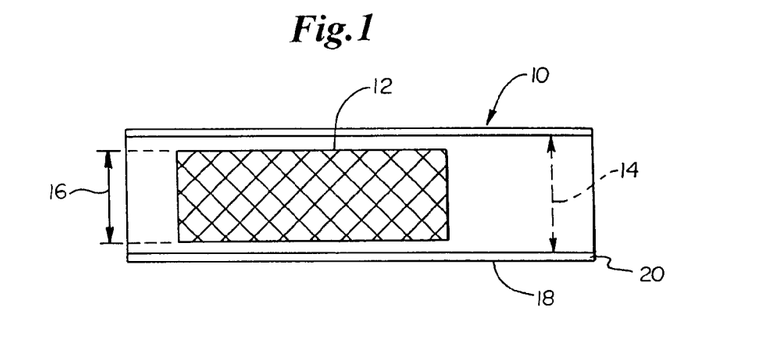
FIG. 1 is a longitudinal cross-sectional view of an embodiment of the invention.

As may be seen in FIG. 1, in some embodiments the present invention is directed to a stent protector or sleeve 10 into which a stent 12 is positioned or placed. The protector is sized to readily accommodate passage of the stent 12 therein. The protector 10 has an inner diameter 14 that is greater than the outer diameter 16 of the stent 12 positioned therein, as a result the protector 10 is provided with a sufficient amount of diameter clearance to allow the stent to pass freely inside the protector 10.

The protector 10 comprises a substantially tubular wall 20 that defines a thickness of about 0.001 inches or thinner and may in some embodiments be in the range of 0.00025 inches or less.

The protector 10 may be constructed of a variety of material selected on the basis of bio-compatibility, tensile strength, impervious structure, and resistance to low temperature cracking if it becomes subject to crumpling or tight folding. Some examples of suitable material or materials from which the protector 10 may be constructed include, but are not limited to: polyethylene terephthalate (PET), polythene and polyethylenes (PE), etc. In some embodiments the protector 10 is at least partially constructed of a heat shrink material.

As is shown in FIG. 1, the protector sleeve 10 is longer than the stent 12 and is configured to be positioned relative to the stent 12 so that at least one end of the protector 10 defines an extension 18 which extends beyond at least one end of the stent 12.

Figure 2:
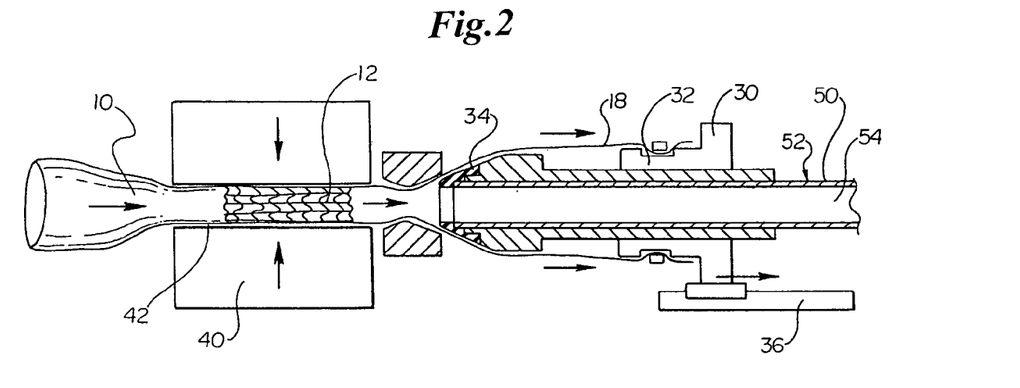
FIG. 2 is a longitudinal cross-sectional view of an embodiment of the invention including a mould assembly, protector and loading device shown in cooperative use for loading a stent onto a catheter.

As is shown in FIG. 2, the extension 18 of the protector 10 is constructed and arranged to engage a protector retaining region 32 of a stent loading tool 30, which is distributed about a stent retaining sheath 52 of a catheter 50.

In the embodiment shown in FIG. 2 the stent 12 and a portion of the protector 10 are positioned within the contracting chamber or iris 42 of a stent contracting assembly or mould 40 for reducing the diameter of the stent 12. The mould 40 may be any type of contracting or crimping device suitable for use in reducing the diameter of a stent or other substantially tubular member.

The extension 18 of the protector 10 is positioned or drawn externally from the iris 42 and is engaged to the protector retaining region 32 of the stent loading tool 30.

Figure 3:
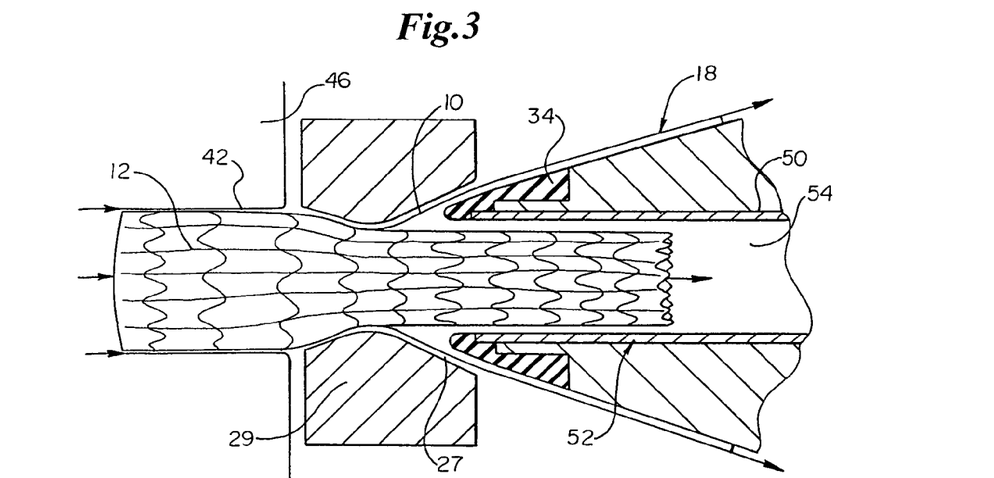
FIG. 3 is a close-up view of a portion of the embodiment shown in FIG. 2.

As is best shown in FIG. 3, as the extension 18 extends from the mould 40 to the protector retaining region 32 of the loading tool 30, the extension 18, and eventually the entire protector 10, is drawn over a tip portion 34 of the loading tool 30. The tip portion 34 allows the stent 12 to pass into the lumen 54 defined by the stent retaining sheath 52 while drawing the protector 10 over and away from the stent and catheter 50. In this manner the stent 12 may be placed directly onto a catheter even if the catheter is not equipped with a retaining sheath.

In some embodiments such as are shown in FIGS. 2 and 3 the protector 10 passes through a profile reducing opening 27 of a stripping head or die 29 before being engaged to the protector retaining region 32 of the stent loading tool 30. Stripping die 29 ensures that the stent 12 is smoothly contracted to a size smaller than the inside diameter of the catheter sheath 52 and to give precise control of the protector 10 as it is stripped off of the stent 12. Though the stripping die 29 provides improved control and removal of the protector 10 from the stent 12, as the stent 12 is advanced into the catheter 50, the use of the stripping die 29 is not required to remove the protector 10 from the stent 12 or to insert the stent 12 into the catheter 50.

As is shown in FIG. 2 the loading tool 30 is moveably or slidingly engaged to a linear slide 36 which provides the tool 30 with the capability of being moved in a liner or longitudinal direction relative to the catheter 50. As the tool 30 slides longitudinally relative to the stationary catheter 50 about which the tool 30 is disposed, the tool 30 as well as the protector 10 and stent 12, engaged thereto via extension 18, are advanced along. As a result, as the stent 12 is guided into the lumen 54 of the retaining sheath 52 and the protector 10 is removed from about the stent 12 in the manner depicted in FIG. 3.

Figure 4:
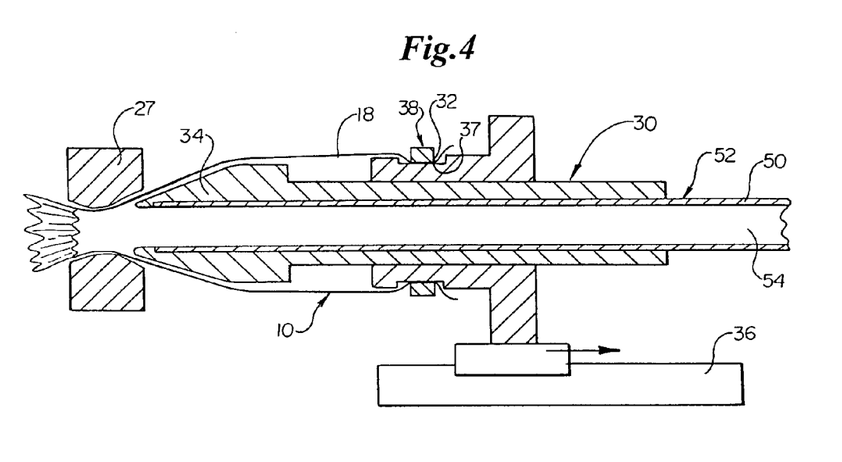
FIG. 4 is a close-up view of a portion of the embodiment shown in FIG. 2

The particular manner in which extension 18 of the protector 10 is engaged to the protector retaining region 32 of the stent loading tool 30 may be varied. However, in the embodiment shown in FIG. 4, the protector retaining region 32 comprises a mechanical engagement comprising a retaining surface 37 about which the extension 18 is disposed and a retaining ring 38 is fitted thereon. The extension 18 is retained to the loading tool 30 by the interface of the surface 37, ring 38 and extension 18 held therebetween. Alternatively, the extension 18 may be adhesively engaged to the retaining region 32, or be otherwise chemically, mechanically or physically engaged thereto.

In the various embodiments of the invention the stent 12 may be any type of stent, graft, stent-graft, filter or other implantable medical device. In at least one embodiment the stent 12 is a "drug delivery" stent having one or more coatings or delivery mechanisms which provide the stent with the ability to transport a therapeutic agent or other substance to a legion site within the body of a patient. Because many stents employ an external coating or coatings of one or more therapeutic or other agents, the protector 10 disposed about the stent 12 will often come in contact and may even retain some residual portion of one or more coatings on its inside surface. As a result, in at least one embodiment the protector 10 is disposable and a new protector 10 is used for each stent loading procedure.

As is clear form the embodiment shown in FIG. 3, when the protector 10 is drawn over the tip portion 34 of the loading tool 30 some of the residual stent coating may be deposited on the tip portion 34 of the tool 30.

In order to reduce the potential of cross contamination of multiple stents being loaded on to a number of catheters, in some embodiments the tip portion 34 of the loading tool 30 is disposable. Alternatively, a used tip 34 may be cleaned and sterilized and then refitted on the loading tool 30 as desired. In at least one embodiment the tip 34 is at least partially constructed from a low surface friction material such as stainless steel, PTFE, etc. In some embodiments the tip comprises a cone angle of about 10 to about 60 degrees. Preferably, the cone angle of the tip 34 is about 20 degrees to about 45 degrees.

Figure 5:
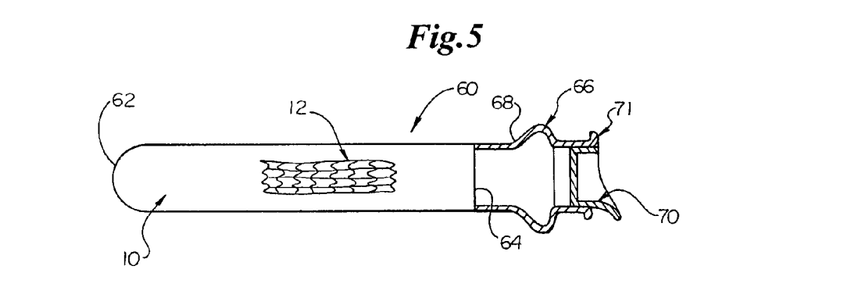
FIG. 5 is a longitudinal cross-sectional view of the embodiment of the invention shown in FIG. 1 wherein the protector is configured as a disposable long term storage capsule.
Figure 6:
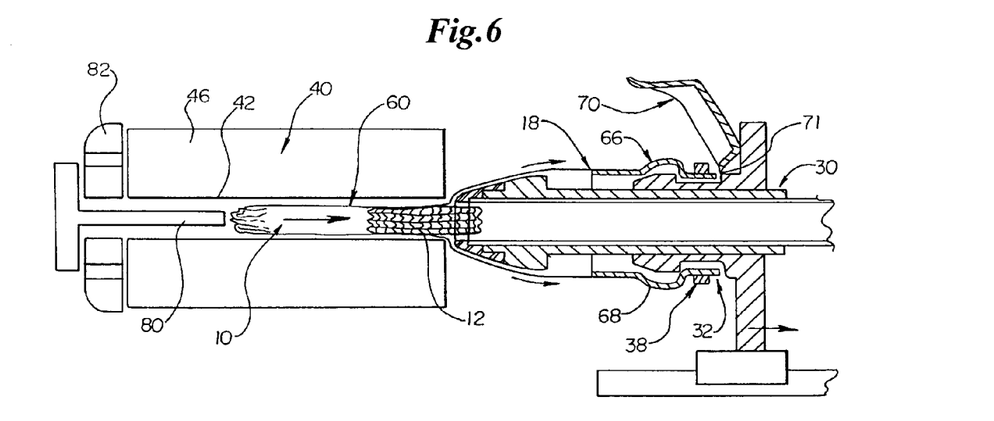
FIG. 6 is a longitudinal cross-sectional view of the capsule of FIG. 5 shown in use with the mould assembly and loading device of FIG. 2

As indicated above, in some embodiments of the invention the protector 10 may be utilized as a disposable and sealable stent storage capsule, such as is indicated generally at 60 in FIG. 5. A capsule 60 comprises a protector sleeve 10 which is sealed at one end 62 and comprises a seal assembly 66 at the opposing open end 64. Assembly 66 includes a seal housing 68 engaged to the open end 64 of the protector 10. The seal housing 68 may be considered to define at least a portion of the protector extension 18. An end cap 70 is removably engaged to the seal housing 68. In at least one embodiment of the invention the end cap 70 is pivotally engaged to the housing 68, at a pivot 71 as is illustrated in FIG. 6. When the cap 70 is removed from the seal housing 68 the stent 12 may be accessed in the manner previously described.

As is shown in FIG. 6 the seal assembly 66 provides the capsule 60 with a ready mechanism for engaging the seal housing 68 of the extension 18 directly to the protector retaining region 32 of the stent loading tool 30. A ring 38 or any other desired mechanism may be utilized to engage the housing 68 of the open capsule 60 to the loading tool 30.

When the stent 12 and protector 10 are positioned within the contracting mould 40, the stent will often be supported by a mandrel 80. Mandrel 80 may be incorporated into or positioned adjacent to an iris chilling system 82, which acts to chill the iris 42 and thus the stent 12 prior to contraction within the mould 40.

Figure 7:
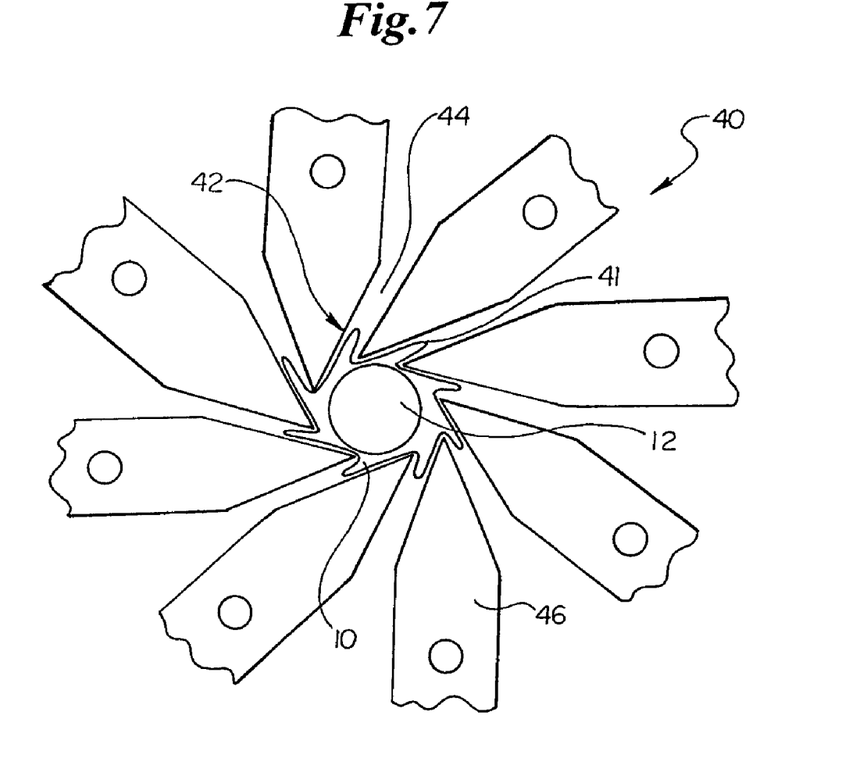
FIG. 7 is a partial cross-sectional view of a mould assembly shown during the contracting process of the stent and protector of FIG. 1.

In addition to the above, a significant advantage that the protector 10, as described herein provides, is that when the stent 12 is contracted via mould 40, such as is shown in FIG. 7, and the diameter of the stent 12 is reduced, the protector 10 is readily deformable so that any excess of slack exhibited by the protector 10 may be formed into one or more folds 41 which may be pulled, or otherwise drawn away from the stent 12 into one or more spaces 44 between the individual contracting members or blades 46 of the iris 42.

Figure 8:
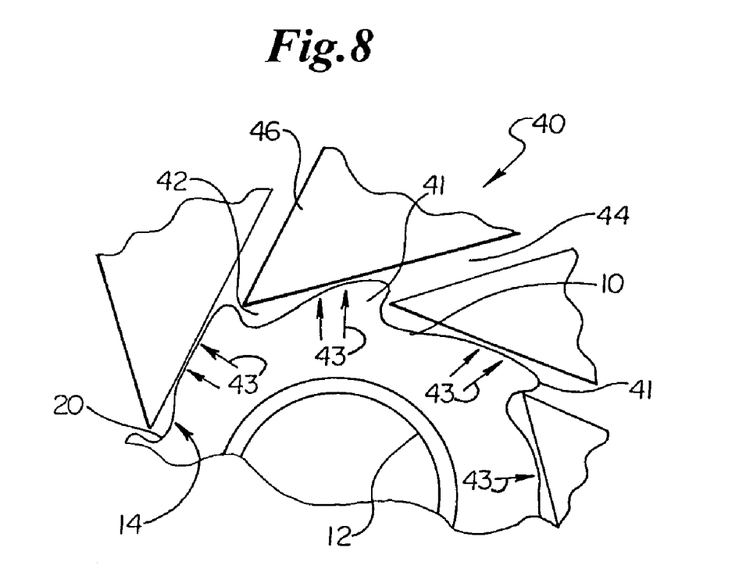
FIG. 8 is a partial view of the embodiment shown in FIG. 7 depicting an example of how the folds of the protector are formed and accommodated by the mould assembly.

In some embodiments, an example of which is shown in FIG. 8 the mould 40 is provided with an internal air pressure which applies a predetermined force or pressure, indicated by arrows 43, against the inner diameter 14 of the protector wall 20. As a result, the protector 10 is held against the blades 46 through out the contracting process. As the stent 12 is contracted, the folds 41 of the protector 10, which form as a result of the diameter of the stent 12 diminishing, are pushed or drawn into the spaces 44 between the blades 46 as a result of the force 43 applied by the internal pressure within the protector 10. In some embodiments a negative pressure, such as provided by a vacuum may be provided to the spaces 44 between the blades 46 in order to draw or pull the folds 41 into the spaces 44.

It should be noted that in at least one embodiment, prior to subjecting the stent 12 and protector 10 to the advancement described herein, the stent is cooled or chilled to a desired temperature and fully contracted by the mould 40. Following this cooling and contracting process, the stent 12 and protector 10 are advanced in the manner described.

Figure 9:
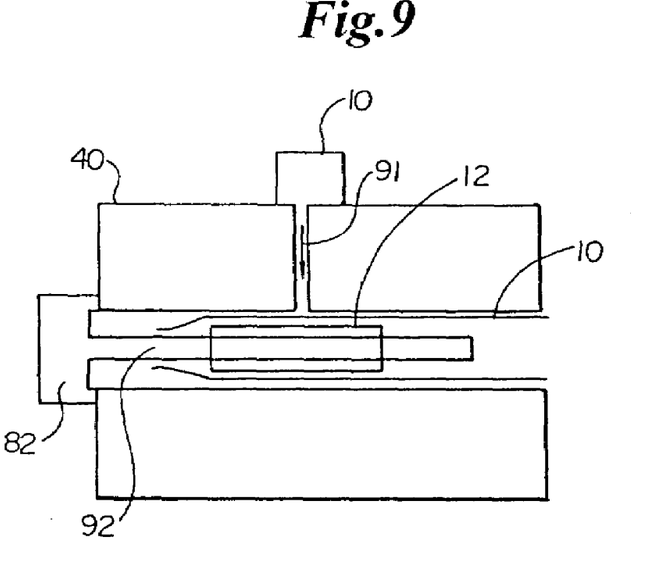
FIG. 9 is a side view of the embodiment shown in FIG. 7 wherein the mould assembly comprises a cooling mechanism.
Figure 11:
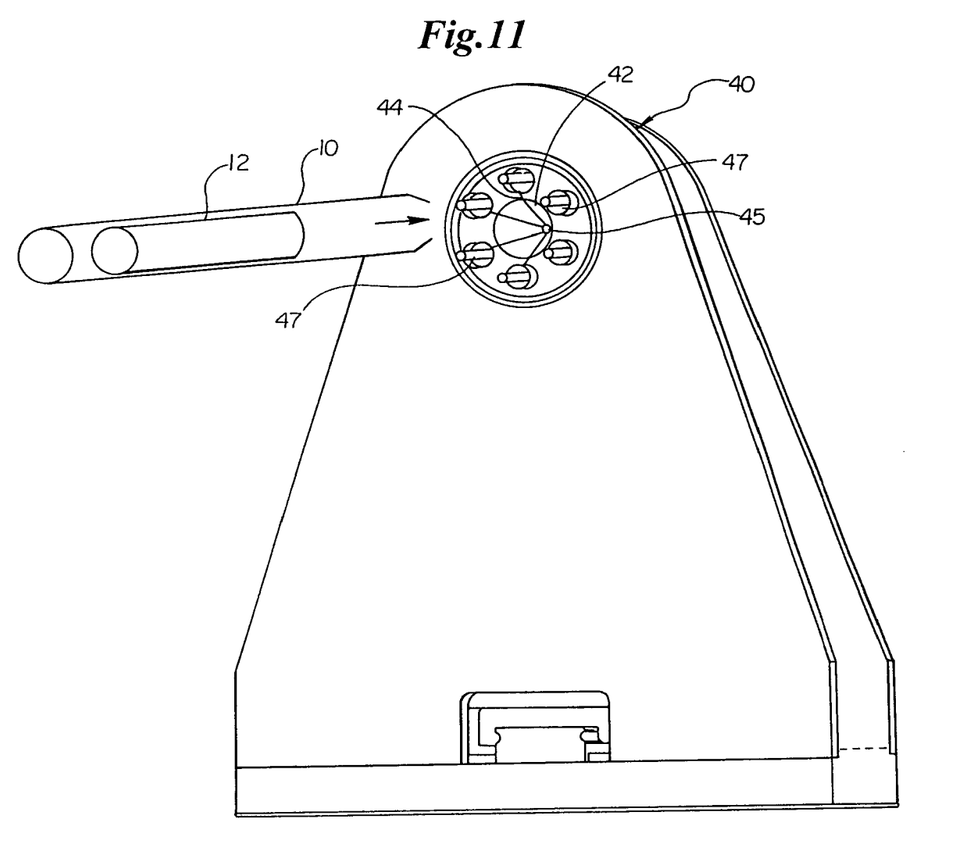
FIG. 11 is a perspective view of an embodiment comprising a mould assembly having a plurality of rollers for drawing the folds of the protector away from the stent as it is reduced in diameter.
Figure 12:
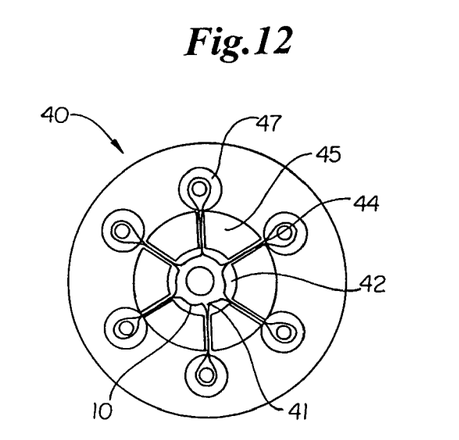
FIG. 12 is a cross-sectional view of the mould assembly wherein the folds of the protector are shown being drawn away from the stent.

In at least one embodiment of the invention the protector 10 has some heat shrink properties or comprises a heat shrink material. A stent 12 and heat shrink protector 10, such as is shown in FIG. 9 may be inserted into the mould 40. The mould 40 may comprise a heating mechanism 90, that injects heated air or other medium, indicated by arrows 91 onto the protector 10. The heat provided by the heated medium 91 provides the protector 10 with sufficient energy to activate the heat shrink properties of the protector 10. As the protector 10 contracts as a result of its heat shrink properties, the folds 41 of the protector 10 are drawn into the spaces 44 between the blades 46, such as shown in FIGS. 7 and 8, or roller members or rods 47 such as are shown in FIGS. 11 and 12.

By providing the protector with heat shrink properties the amount of excess material forming folds as the stent is contracted may be reduced or even eliminated. In embodiments where excess material of the reduced diameter protector is sufficiently minimized so that folds are not formed, or the folds are so insubstantial that they are unable to be drawn between the blades or roller members of the mould it may be necessary to cut and unwrap the protector from the stent following the contracting process.

As is shown in FIG. 9, in some embodiments the mould 40 may be provided with a cooling pipe 92 about which the stent 12 and protector 10 are disposed within the mould 40. The cooling pipe may act as a mandrel 80 as previously described. The cooling pipe 92 may be provided with a reduced temperature relative to the stent 12 to conductively cool the stent 12 to a desired temperature, prior to, during, or subsequent to the contracting process.

Figure 10:
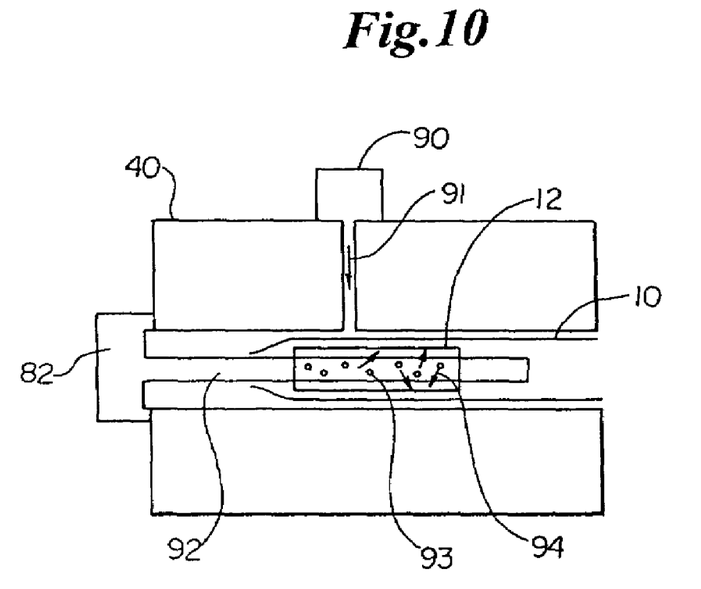
FIG. 10 is a side view of the embodiment shown in FIG. 7 wherein the mould assembly comprises a cooling mechanism.

In at least one embodiment, an example of which is shown in FIG. 10, the cooling pipe 92 defines a plurality of openings or perforations 93 through which a coolant, indicated by arrows 94, such as for example atomized liquid cryogenic fluid, may be injected to directly cool the stent 12 to a desired temperature. The coolant 94 is supplied by the chilling system 82 with which the cooling pipe 92 may be in fluid communication.

Because the cooling pipe 92 is positioned within the stent 12, and it is necessary to remove the stent 12 and protector 10 from the mould 40, the diameter of the cooling pipe 92 must be less than or equal to the inside diameter of the stent 12 after the stent 12 has been contracted by the mould 40.

In some moulds, an example of which is shown in FIG. 11, the mould 40 defines a substantially cone shaped iris 42 of gradually decreasing diameter into which the stent 12 is inserted in order to contract and reduce the diameter of the stent according to the smallest diameter of the iris 42. Iris 42 defines a plurality of spaces 44 each of which extend from the iris opening 45 to a rotatable roller member 47. As shown in FIG. 12, each opening and rod member 47 is constructed and arranged to engage a fold of the protector 10 and as the stent and protector are advanced through the mould 40 the rods 47 rotate to draw the increasing slack of the folds away from the stent 12.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A system for protecting a stent from contact during loading comprising:
   ma stent, the stent having a length and an outer diameter;
   a protective sleeve, the protective sleeve defined by a substantially tubular wall, the substantially tubular wall defining an inner diameter and outer diameter of the protective sleeve, the protective sleeve constructed and arranged to be positioned over the stent, inner diameter of the protective sleeve being greater than the outer diameter of the stent, the protective sleeve having a length, the length of the sleeve being longer than the length of the stent, a portion of the protective sleeve extending beyond the length of the stent defining a sleeve extension;
   a loading tool for loading the stent onto a catheter, the loading tool constructed and arranged to be positioned about at least a portion of a stent retaining sleeve of the catheter, the loading tool defining a tip region, the tip region constructed and arranged to separate the substantially tubular wall of the protective sleeve and the stent from one another when the protective sleeve is pulled over the tip region of the loading tool, when the protective sleeve is pulled over the tip region of the loading tool, the stent is advanced into a lumen defined by the at least a portion of a stent retaining sleeve of the catheter.

2. The system of claim 1 wherein the stent is selected from at least one member of the group consisting of: a self-expandable stent, a balloon expandable stent, a hybrid expandable stent.

3. The system of claim 1 wherein the stent is a drug delivery stent.

4. The system of claim 1 wherein the protective sleeve defines an opening at at least one end.

5. The system of claim 1 wherein the protective sleeve is sealed at at least one end.

6. The system of claim 1 wherein the substantially tubular wall of the protective sleeve defines a wall thickness, the wall thickness being about 0.001 of an inch to about 0.00025 of an inch.

7. The system of claim 1 wherein the substantially tubular wall of the protective sleeve defines a wall thickness, the wail thickness being less than about 0.001 inches.

8. The system of claim 1 wherein the substantially tubular wall of the protective sleeve defines a wall thickness, the wall thickness being less than about 0.0005 inches.

9. The system of claim 1 wherein the substantially tubular wall of the protective sleeve defines a wall thickness, the wall thickness being less than about 0.00025 inches.

10. The system of claim 1 wherein the protective sleeve is at least partially constructed of a biocompatible material.

11. The system of claim 1 wherein the protective sleeve is at least partially constructed of a material resistive to low temperature cracking.

12. The system of claim 1 wherein the protective sleeve is at least partially constructed of a foldable material.

13. The system of claim 1 wherein the protective sleeve is at least partially constructed of at least one material of the group consisting of: polyethylene terephthalate, polythene, polyethylene and any combinations thereof.

14. The system of claim 1 wherein the protective sleeve has a first end and a second end, the first end of the protector comprising the sleeve extension, the sleeve extension constructed and arranged to be receivingly engaged to a sleeve retaining region of the loading tool, the sleeve extension being drawn over the tip region of the loading tool to engage the sleeve retaining region.

15. The system of claim 14 wherein the sleeve retaining region comprises an annular surface of the loading tool and a retaining ring disposed thereabout, when the sleeve extension is engaged to the sleeve retaining region, the sleeve extension is engaged between the annular surface and the retaining ring.

16. The system of claim 14 wherein the second end of the protector is sealed.

17. The system of claim 16 wherein the sleeve extension comprises a seal assembly, the seal assembly defining a seal housing and an end cap, the seal housing defining an opening through which the stent is passed into and out of the protective sleeve, the end cap constructed and arranged to be removably received into and out of the opening defined by the seal housing.

18. The system of claim 17 wherein the end cap is pivotally engaged to the seal housing.

19. The system of claim 1 further comprising a stent contracting assembly, the stent contracting assembly comprising a plurality of contracting members, adjacent contracting members defining a space therebetween, the plurality of contracting members defining a contracting iris, the contracting iris in fluid communication with each space, the contracting assembly constructed and arranged to receive the stent and at least a portion of the protective sleeve positioned thereabout into and through the contracting iris, wherein the stent contracting assembly exerts a contracting action on the stent to reduce the stent from a first diameter to a second diameter when the stent and protective sleeve is positioned therein, the second diameter being less than the first diameter.

20. The system of claim 19 wherein when the stent and protective sleeve are positioned within the contracting iris, the substantially tubular wall of the protective sleeve forms at least one fold.

21. The system of claim 20 wherein when the stent and protective sleeve are positioned within the contracting iris, the at least one fold is drawn radially outward away from the stent through the space defined by adjacent contracting members.

22. The system of claim 21 wherein when the stent and protective sleeve are positioned within the contracting iris, a positive air pressure is supplied to the inside diameter of the substantially tubular wall of the protective sleeve.

23. The system of claim 21 wherein when the stent and protective sleeve are positioned within the contracting iris, each of the spaces defined by the adjacent contracting members is provided with a negative air pressure.

24. The system of claim 21 wherein each of the contracting members is a radially moveably blade, each of the radially moveable blades being moveably from a radially outward position wherein the contracting iris defines a space at least as large as the outer diameter of the protective sleeve when a stent is positioned therein, to a radially inward position wherein the iris defines a space at least as large as the second diameter of the stent.

25. The system of claim 21 wherein the iris is substantially conical in shape.

26. The system of claim 25 wherein the contracting assembly further comprises at least one opening and rod member, the opening and rod member constructed and arranged to engage the at least one fold and draw the at least one fold away from the stent trough the space defined by adjacent contracting members.

27. The system of claim 19 wherein the protective sleeve is at least partially constructed of a material having heat shrink properties.

28. The system of claim 19 wherein the stent contracting assembly further comprises a heating mechanism, the heating mechanism in fluid communication with the contracting iris, the heating mechanism constructed and arranged to transmit a heated medium to the protective sleeve.

29. The system of claim 19 wherein the stent contracting assembly further comprises a cooling pipe, the stent being at least partially disposed about the cooling pipe when the stent and the at least a portion of the protective sleeve positioned thereabout are positioned into the contracting iris, the cooling pipe being constructed and arranged to cool the stent to a predetermined temperature.

30. The system of claim 29 wherein the cooling pipe is in fluid communication with a coolant source, the cooling pipe defines a plurality of coolant openings, the coolant openings constructed and arranged to transmit a coolant to the stent.

31. The system of claim 29 wherein the stent is cooled by conductive contact with the stent.

32. The system of claim 19 wherein when the stent and the at least a portion of the protective sleeve is positioned within the contracting iris, sleeve extension extends from the contracting iris and over the tip region of the loading tool to engage the loading tool at a sleeve retaining region of the loading tool.

33. The system of claim 32 wherein the loading tool is slideably engaged to a slide rail, the slide rail being longitudinally parallel to the at least a portion of a stent retaining sleeve of the catheter.

34. The system of claim 33 wherein the loading tool is constructed and arranged to be moved longitudinally away from the contracting assembly, wherein when the sleeve extension is engaged to the loading tool and the loading tool is moved longitudinally away from the contracting assembly the protective sleeve is drawn over the tip region of the loading tool and the stent is advanced into the lumen of the at least a portion of a stent retaining sleeve of the catheter.

35. The system of claim 32 further comprising a stripping head, the striping head being positioned between the contracting assembly and the loading tool, the stripping head defining a stripping opening, the stripping head constructed and arranged to pass the stent and the at least a portion of the protective sleeve as they exit the contracting iris.

36. The system of claim 1 wherein the tip region is removable from an adjacent portion of the loading tool.

37. The system of claim 36 wherein the tip region is disposable.

* * * * *